United States Patent
Xu

(10) Patent No.: US 7,440,550 B2
(45) Date of Patent: Oct. 21, 2008

(54) COLLIMATOR X-RAY IRRADIATOR AND X-RAY APPARATUS

(75) Inventor: Xiaodong Xu, Beijing (CN)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 138 days.

(21) Appl. No.: 10/579,899

(22) PCT Filed: Nov. 20, 2003

(86) PCT No.: PCT/CN03/00986

§ 371 (c)(1),
(2), (4) Date: May 19, 2006

(87) PCT Pub. No.: WO2005/048846

PCT Pub. Date: Jun. 2, 2005

(65) Prior Publication Data

US 2007/0086575 A1    Apr. 19, 2007

(51) Int. Cl.
*G21K 1/02* (2006.01)
*G21K 1/04* (2006.01)

(52) U.S. Cl. .................. 378/147; 378/148; 378/150

(58) Field of Classification Search ................ 378/145, 378/147–153, 160, 161
See application file for complete search history.

(56) References Cited

U.S. PATENT DOCUMENTS

| | | | |
|---|---|---|---|
| 4,200,803 A | 4/1980 | Becker et al. | |
| 4,277,685 A | 7/1981 | Covic et al. | |
| 4,419,585 A | 12/1983 | Strauss et al. | |
| 4,506,374 A * | 3/1985 | Flynn | 378/2 |
| 5,396,534 A * | 3/1995 | Thomas | 378/160 |
| 5,436,958 A | 7/1995 | Taylor | |
| 5,438,454 A | 8/1995 | Ludewigt et al. | |
| 5,748,703 A * | 5/1998 | Cosman | 378/152 |
| 6,052,430 A | 4/2000 | Siochi et al. | |

(Continued)

FOREIGN PATENT DOCUMENTS

JP    2002-355242    12/2002

(Continued)

OTHER PUBLICATIONS

Xiaodong Xu et al.; Patent Application "Collimator, X-Ray Irradiator, And X-Ray Apparatus" filed Nov. 4, 2004; U.S. Appl. No. 10/982,114;17 pgs.

*Primary Examiner*—Irakli Kiknadze
(74) *Attorney, Agent, or Firm*—Armstrong Teasdale LLP

(57) ABSTRACT

A collimator is to be provided which permits the reduction of size without using any special material and without sacrificing an aperture. To this end, the collimator comprises: a pair of first plate members each having X-ray absorbability, movable in a direction parallel to a surface thereof, and defining an X-ray passing aperture by a spacing between respective mutually opposed end faces; and a pair of second plate members each having X-ray absorbability, the second block members, in order to block other X-rays than the X-ray passing through the aperture, being connected at respective one ends by hinges to end portions of the pair of first plate members opposite to the mutually opposed end faces of the first plate members and being supported at respective opposite ends so as to be movable obliquely with respect to the moving direction of the first plate members with movement of the first plate members.

20 Claims, 7 Drawing Sheets

U.S. PATENT DOCUMENTS

| | | |
|---|---|---|
| 6,108,400 A | 8/2000 | Siochi |
| 6,330,300 B1 | 12/2001 | Siochi |
| 6,449,340 B1 | 9/2002 | Tybinkowski et al. |
| 6,788,764 B2 | 9/2004 | Saladin et al. |
| 6,850,596 B2 * | 2/2005 | Sundermann et al. ....... 378/147 |
| 2002/0057761 A1 | 5/2002 | Danielsson |

FOREIGN PATENT DOCUMENTS

| WO | WO-01/54137 A1 | 7/2001 |
|---|---|---|

* cited by examiner

COLLIMATOR X-RAY IRRADIATOR AND X-RAY APPARATUS

CROSS REFERENCE TO RELATED APPLICATIONS

This application claims the benefit of PCT/CN2003/000986 filed Nov. 20, 2003.

BACKGROUND OF THE INVENTION

The present invention relates to a collimator, as well as an X-ray irradiator and an X-ray apparatus. Particularly, the invention is concerned with a collimator for restricting an irradiation range of X-ray, as well as an X-ray irradiator and an X-ray apparatus both provided with such a collimator.

In an X-ray irradiator there is used a collimator for restricting an irradiation range of X-ray. The collimator has an aperture permitting X-ray to pass therethrough and has a structure such that X-ray cannot pass through the collimator except the aperture. With this structure, the irradiation range of X-ray can be adjusted.

A collimator having a variable aperture is provided with movable plate members, that is, blades having X-ray absorbability. As the blades there are used a pair of blades opposed to each other at respective end faces. The pair of blades are movable in directions opposite to each other in a plane parallel to their surfaces. For expanding the aperture, the pair of blades are moved in directions away from each other, while for narrowing the aperture, the blades are moved toward each other.

As a collimator developed for reducing the size thereof without sacrificing a variable range of an aperture there is known one in which blades are constructed of a flexible material and are wound round drums and, for expanding the aperture, are wound inwards round the drums, while for narrowing the aperture, they are paid out from the drums (see, for example, Patent Literature 1).

[Patent Literature]

Japanese Published Unexamined Patent Application No. 2002-355242 (pages 2 to 3, FIGS. 1 to 2)

The above known collimator involves the problem that it is necessary to use a special material flexible and superior in X-ray absorbability as the blase material.

SUMMARY OF THE INVENTION

Therefore, it is an object of the present invention to provide a collimator which can be reduced in size without using any special material and without sacrificing an aperture, as well as an X-ray irradiator and an X-ray apparatus both provided with such a collimator.

(1) The present invention, in one aspect thereof for solving the above-mentioned problem, resides in a collimator comprising: a pair of first plate members each having X-ray absorbability, movable in a direction parallel to a surface thereof, and defining an X-ray passing aperture by a spacing between respective end faces opposed to each other; and a pair of second plate members each X-ray absorbability, the second plate members, in order to block other X-rays than the X-ray passing through the aperture, being connected at respective one ends by hinges to end portions of the pair of first plate members opposite to the mutually opposed end faces of the first plate members and being supported at respective opposite ends so as to be movable obliquely with respect to the moving direction of the first plate members with movement of the first plate members.

(2) The present invention, in another aspect thereof for solving the above-mentioned problem, resides in an X-ray irradiator comprising: an X-ray tube; and a collimator for collimating X-ray generated from the X-ray tube. The collimator comprises: a pair of first plate members each having X-ray absorbability, movable in a direction parallel to a surface thereof, and defining an X-ray passing aperture by a spacing between respective end faces opposed to each other; and a pair of second plate members each having X-ray absorbability, the second plate members, in order to block other X-rays than the X-ray passing through the aperture, being connected at respective one ends by hinges to end portions of the pair of first plate members opposite to the mutually opposed end faces of the first plate members and being supported at respective opposite ends so as to be movable obliquely with respect to the moving direction of the first plate members with movement of the first plate members.

(3) The present invention, in a further aspect thereof for solving the above-mentioned problem, resides in an X-ray apparatus comprising: an X-ray tube; a collimator for collimating X-ray generated from the X-ray tube and applying the collimated X-ray to an object to be radiographed; and a detector means for detecting the X-ray which has passed through the object to be radiographed. The collimator comprises: a pair of first plate members each having X-ray absorbability, movable in a direction parallel to a surface thereof, and defining an X-ray passing aperture by a spacing between respective end faces opposed to each other; and a pair of second plate members each having X-ray absorbability, the second plate members, in order to block other X-rays than the X-ray passing through the aperture, being connected at respective one ends by hinges to end portions of the pair of first plate members opposite to the mutually opposed end faces of the first plate members and being supported at respective opposite ends so as to be movable obliquely with respect to the moving direction of the first plate members with movement of the first plate members.

In the invention in each of the above aspects, the second plate members which constitute blades together with the first plate members are bent from connections and are movable obliquely, so that an external form of the collimator can be made small without using any special material such as a flexible X-ray absorbing material and without sacrificing the aperture.

From the standpoint of simplifying the support structure it is preferable that the opposite ends of the second plate members be supported by guide grooves formed obliquely relative to the moving direction of the first plate members and pins engaged in the guide grooves. Likewise, from the standpoint of enhancing the freedom of setting an irradiation range in the moving direction of the first plate members it is desirable that the pair of first plate members be movable independently of each other.

According to the present invention, it is possible to provide a collimator which permits the reduction of size, as well as an X-ray irradiator and an X-ray apparatus both provided with such a collimator, without using any special material and without sacrificing the aperture.

Further objects and advantages of the present invention will be apparent from the following description of the preferred embodiments of the invention as illustrated in the accompanying drawings.

DETAILED DESCRIPTION OF THE INVENTION

Figure 1:
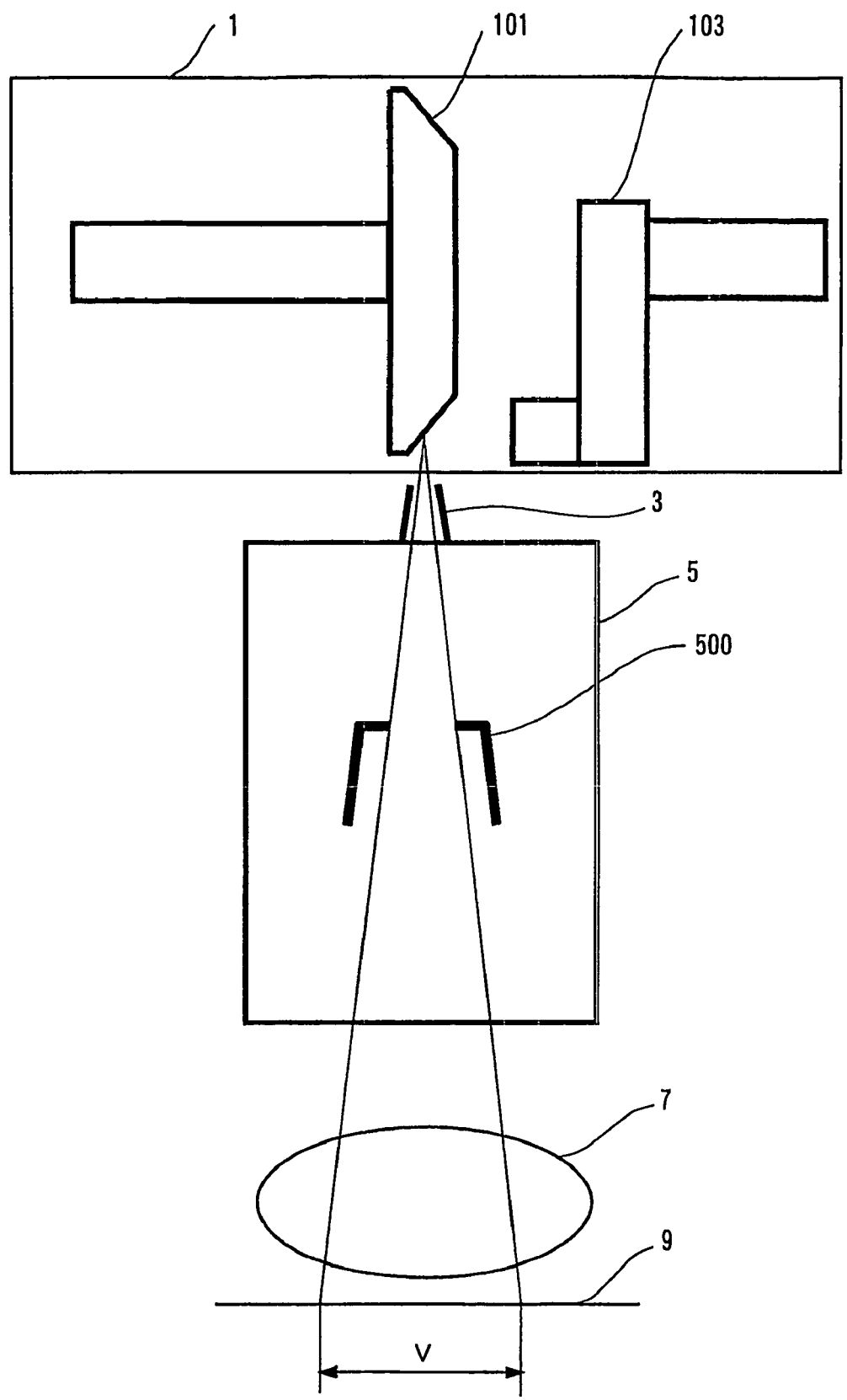
FIG. 1 illustrates a schematic construction of an X-ray apparatus.

An embodiment of the present invention will be described in detail hereinunder with reference to the drawings. FIG. 1 illustrates an X-ray apparatus schematically. This apparatus is an example of a mode for carrying out the invention. With the construction of this apparatus there is shown an example of a mode for carrying the invention with respect to the apparatus thereof.

In this X-ray apparatus, as shown in the same figure, X-ray generated from an X-ray tube 1 is diaphragmed by an X-ray diaphragm 3 and is collimated by a collimating plate 500 disposed within a collimator 5, then the collimated X-ray is applied toward an object 7 to be radiographed and transmitted X-ray is detected by a detector 9. The X-ray tube 1 is an example of a mode for carrying out the invention with respect to the X-ray tube defined herein. The collimator 5 is an example of a mode for carrying out the invention with respect to the collimator of the invention. The detector 9 is an example of a mode for carrying out the invention with respect to the detector means defined herein.

The portion comprising the X-ray tube 1, X-ray diaphragm 3 and collimator 5 is an example of a mode for carrying out the invention with respect to the X-ray apparatus of the invention. With the construction of this apparatus there is shown an example of a mode for carrying out the invention with respect to the X-ray apparatus of the invention. The collimator 5 is an example of a mode for carrying out the invention with respect to the collimator of the invention. With the construction of this apparatus there is shown an example of a mode for carrying out the invention with respect to the collimator of the invention.

The X-ray tube 1 has an anode 101 and a cathode 103, and X-ray is generated from a point of collision (focus) of electrons which are emitted from the cathode 103 toward the anode 101. The X-ray thus generated is applied to the object through the X-ray diaphragm 3 and the collimator 5. The X-ray diaphragm 3 is constructed of an X-ray absorbing material such as lead for example. The collimating plate 500 in the collimator 5 is also constructed of an X-ray absorbing material such as lead for example.

The X-ray diaphragm 3 shapes the X-ray generated from the X-ray tube 1 so that the X-ray becomes a quadrangular pyramid-like beam with an X-ray focus on the anode 101 as a vertex. The collimator 5 defines an X-ray irradiation field V by an aperture which is formed by the collimating plate 500. The aperture is variable to adjust the X-ray irradiation field V.

Figure 2:
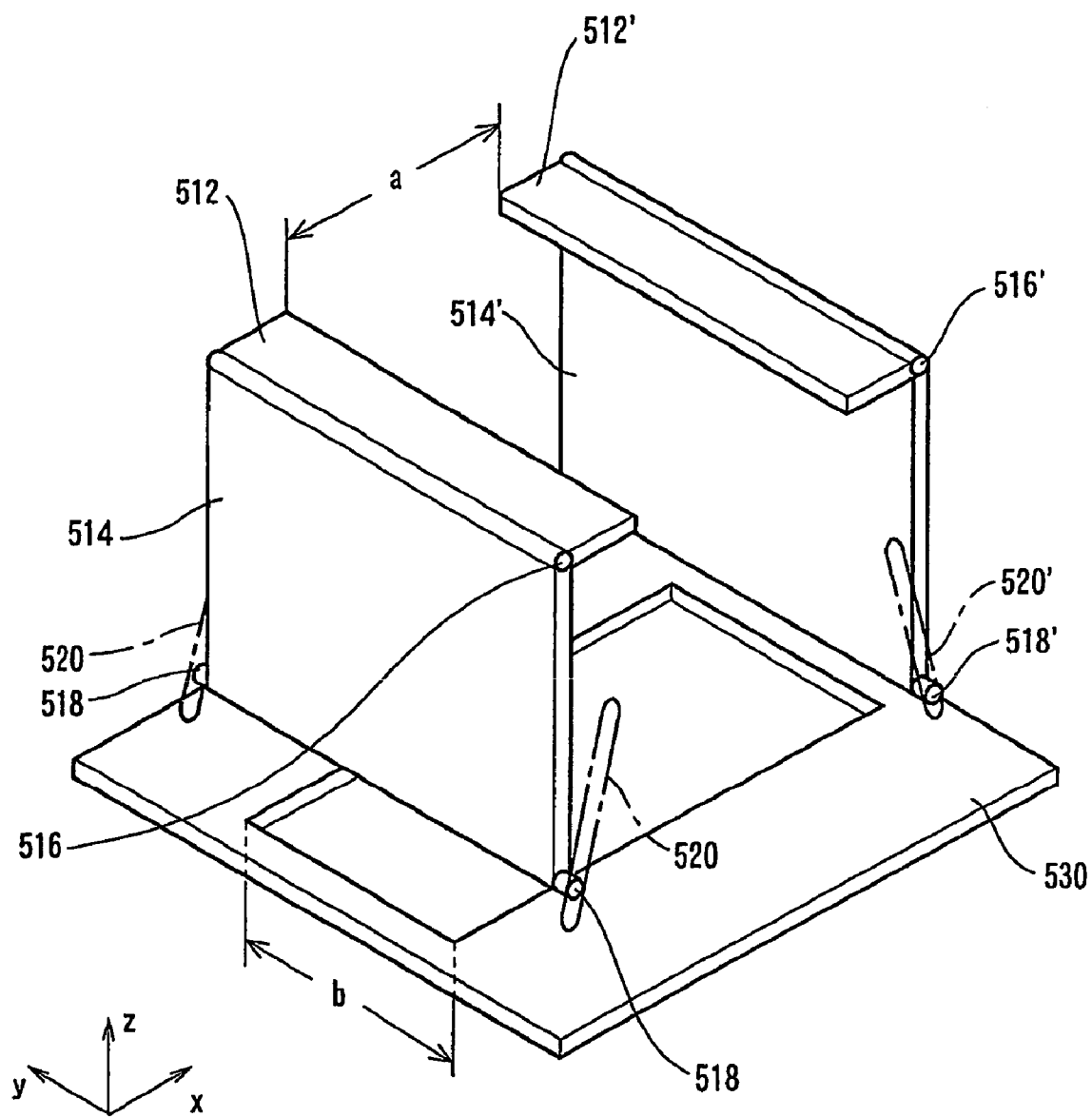
FIG. 2 illustrates the construction of a principal portion of a collimating plate.

Reference will be made to the collimating plate 500 in the collimator 5. FIG. 2 shows the construction of a principal portion of the collimating plate 500. In the same figure, three mutually perpendicular directions are assumed to be x, y, and z directions, z being the vertical direction. The X-ray is radiated from above.

As shown in the same figure, the collimating plate 500 has a pair of horizontal plates 512 and 512'. The horizontal plates 512 and 512' are rectangular plates and are constructed of an X-ray absorbing material such as lead for example. The horizontal plates 512 and 512' lie on the same plane and their long sides are parallel to each other, while their short sides corresponding to each other lie on the same straight lines respectively. The horizontal plates 512 and 512' are displaceable in their short side direction (x direction), whereby a distance "a" between their mutually opposed end faces can be adjusted. The horizontal plates 512 and 512' are an example of a mode for carrying out the invention with respect to the first plate members defined herein.

Figure 3:
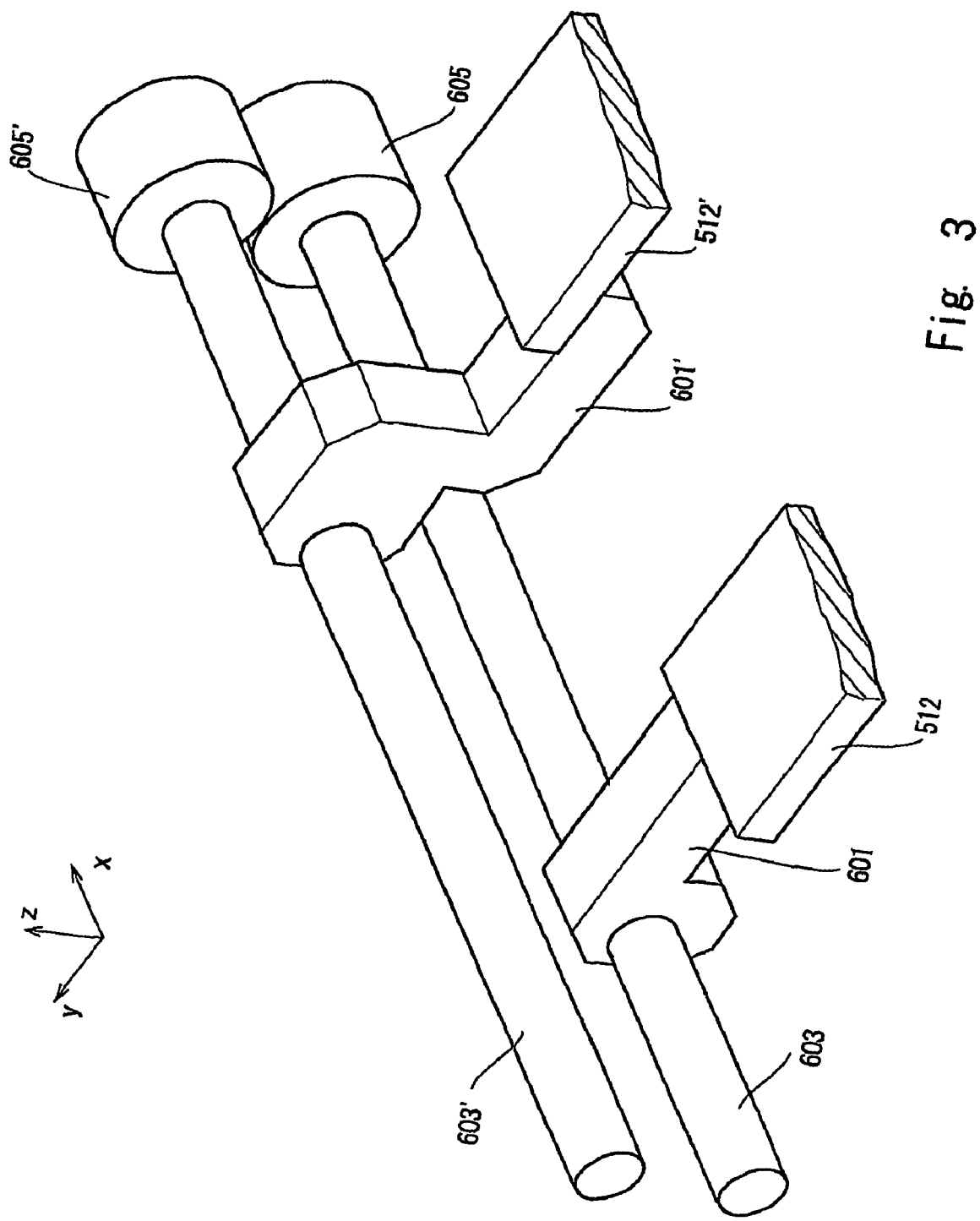
FIG. 3 illustrates the construction of a drive mechanism.

The horizontal plates 512 and 512' are position-adjustable independently of each other. An example of a drive mechanism which permits such a positional adjustment is shown in FIG. 3. As shown in the same figure, the horizontal plates 512 and 512' have arms 601 and 601', respectively, which extend in y direction. The arms 601 and 601' are engaged at end portions thereof with shafts 603 and 603', respectively.

The shafts 603 and 603' are parallel shafts extending in x direction and spaced a predetermined interval from each other in z direction. The arm 601' is bent to equalize the height of the horizontal plate 512' with that of the horizontal plate 512 in z direction.

The shafts 603 and 603' are threaded throughout the overall length thereof. Engaging portions of the arms 601 and 601' with the shafts 603 and 603' are correspondingly threaded internally. Motors 605 and 605' are mounted on one ends of the shafts 603 and 603', respectively. The motor 605 is a reverse-rotatable motor. The motors 605 and 605' are controlled each independently by a control means (not shown).

A pair of follow-up plates 514 and 514' are connected to the horizontal plates 512 and 512', respectively. One ends of the follow-up plates 514 and 514' are connected through hinges 516 and 516' respectively to end faces of the horizontal plates 512 and 512' on the side opposite to the mutually opposed end faces of the horizontal plates, while their opposite ends are engaged in guide grooves 520 and 520' through pins 518 and 518', respectively.

The pins 518 and 518' project in y direction from the opposite ends of the follow-up plates 514 and 514'. The guide grooves 520 and 520' with those pins engaged therein are formed in a plate (not shown) which is opposed to the end faces in y direction of the follow-up plates 514 and 514'. The guide grooves 520 and 520' are oblique to have a shape of inwardly inclined two lines in an xz plane. The inclination of the guide grooves 520 and 520' is determined so as to run along the outer periphery of the quadrangular pyramid beam formed by the X-ray diaphragm 3.

The pair of follow-up plates 514 and 514' are also constructed of an X-ray absorbing material such as lead for example. The hinges 516 and 516' are also formed of lead for example to block the passage of X-ray. The follow-up plates 514 and 514' are one example of a mode for carrying out the invention with respect to the second plate member of the invention.

A window plate 530 is disposed horizontally below the follow-up plates 514 and 514'. The window plate 530 has a square window. As to the size of the window, it takes a fixed value "b" in y direction, while in x direction it takes a fixed value larger than a maximum value of the spacing "a" between the horizontal plates 512 and 512'.

Figure 4:
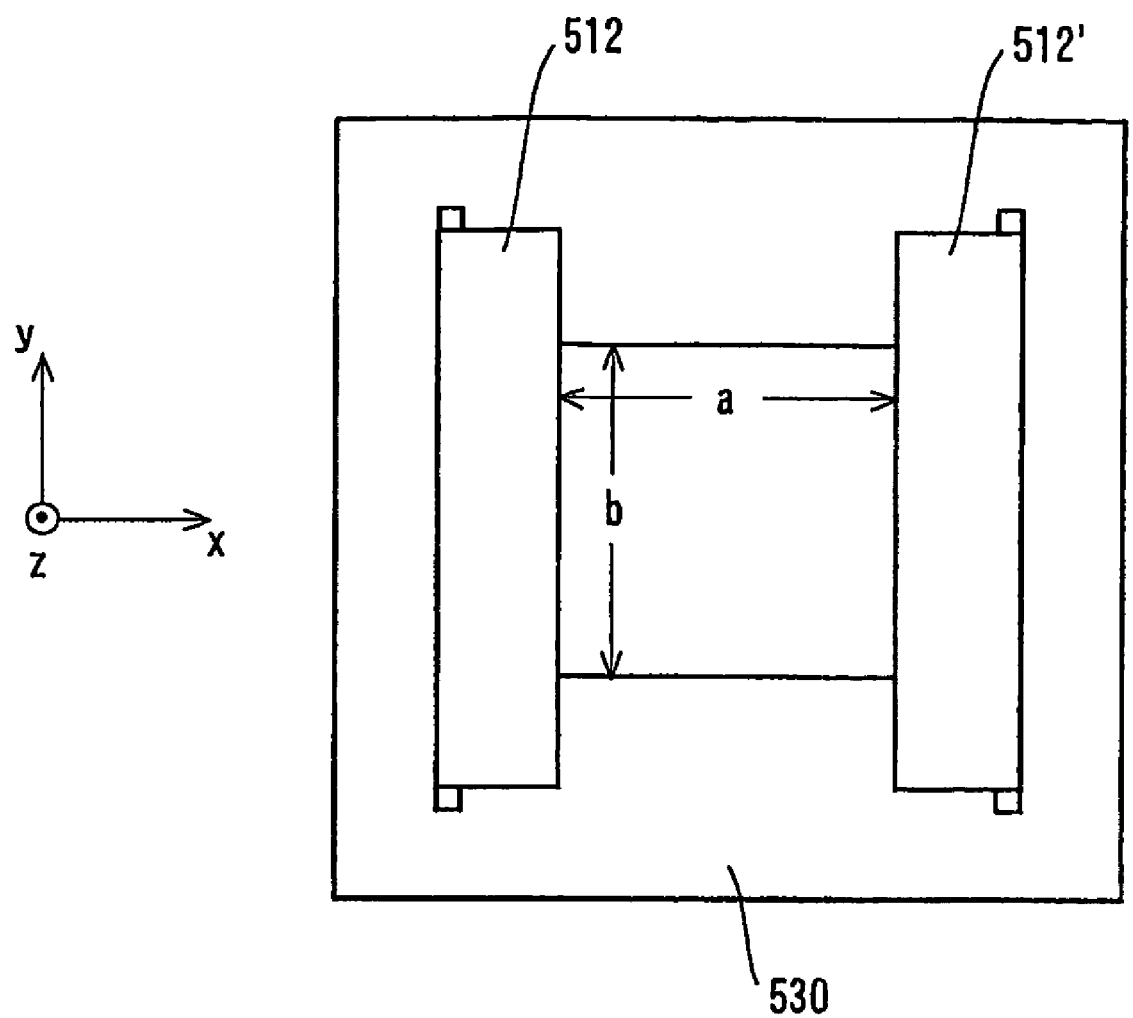
FIG. 4 illustrates in what state an aperture is formed.

With the collimating plate 500 of such a construction, as shown in FIG. 4, there is formed a quadrangular aperture having a size of a×b for the X-ray emitted from the X-ray tube 1. Since the positions of the horizontal plates 512 and 512' can be changed, the size "a" in x direction of the aperture can be adjusted as desired.

Figure 5:
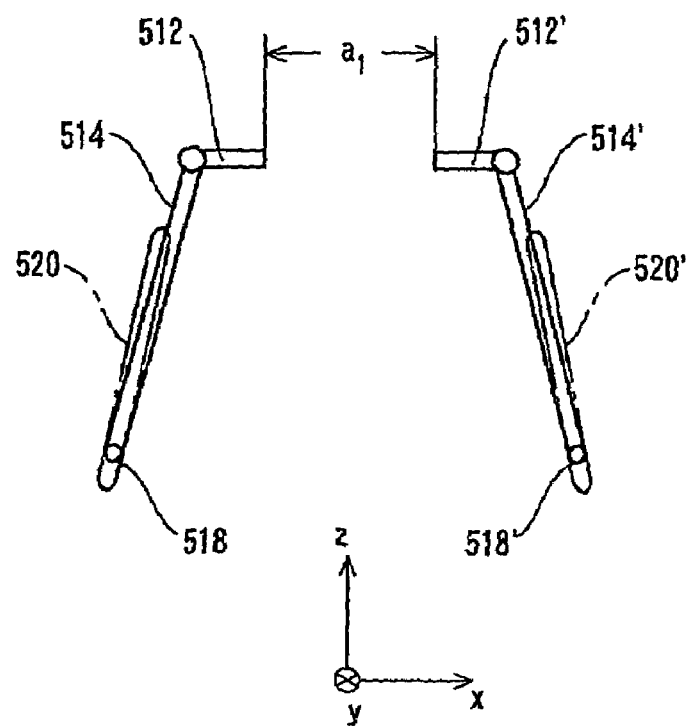
FIG. 5 illustrates adjusting the aperture.
Figure 6:
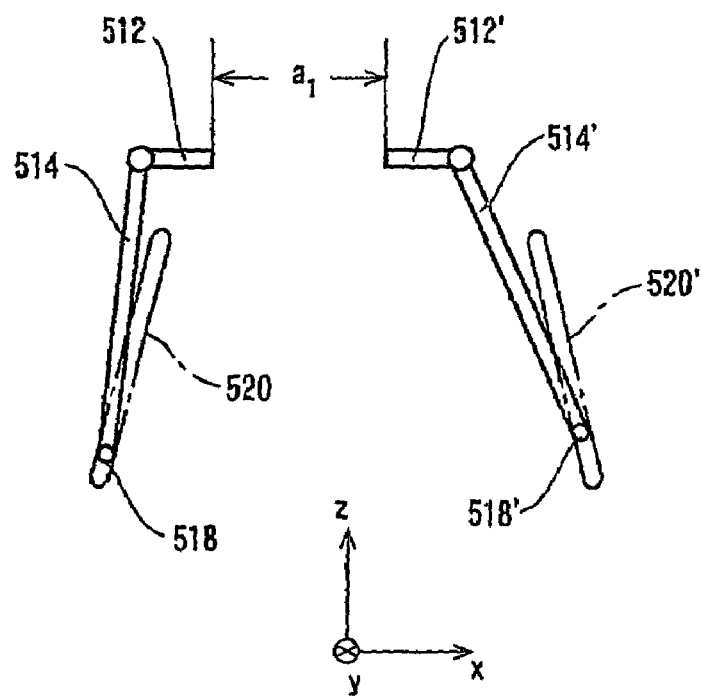
FIG. 6 illustrates adjusting the aperture.

As shown in FIG. 5, the aperture can be set to a desired value a1 by adjusting the spacing between the horizontal plates 512 and 512'. Since the horizontal plates 512 and 512' can be adjusted their positions each independently, it is possible to change the position of the aperture while maintaining the same opening, for example as shown in FIG. 6.

Figure 7:
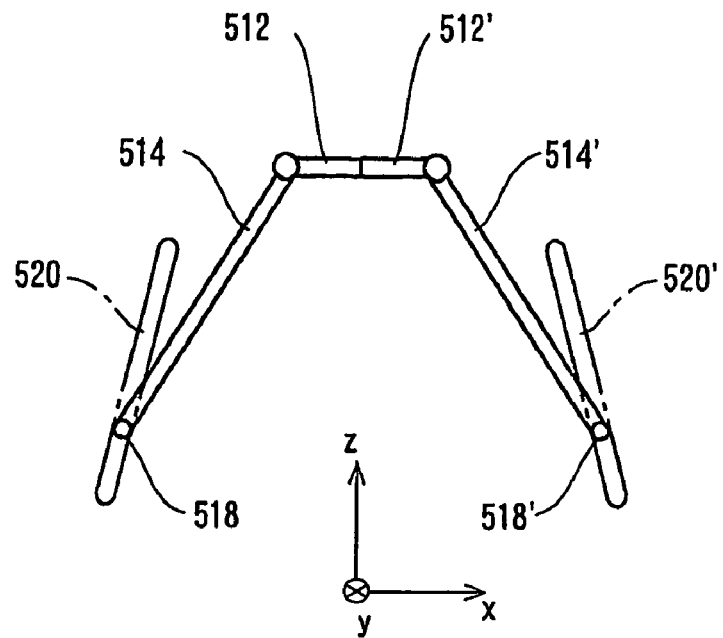
FIG. 7 illustrates adjusting the aperture.
Figure 8:
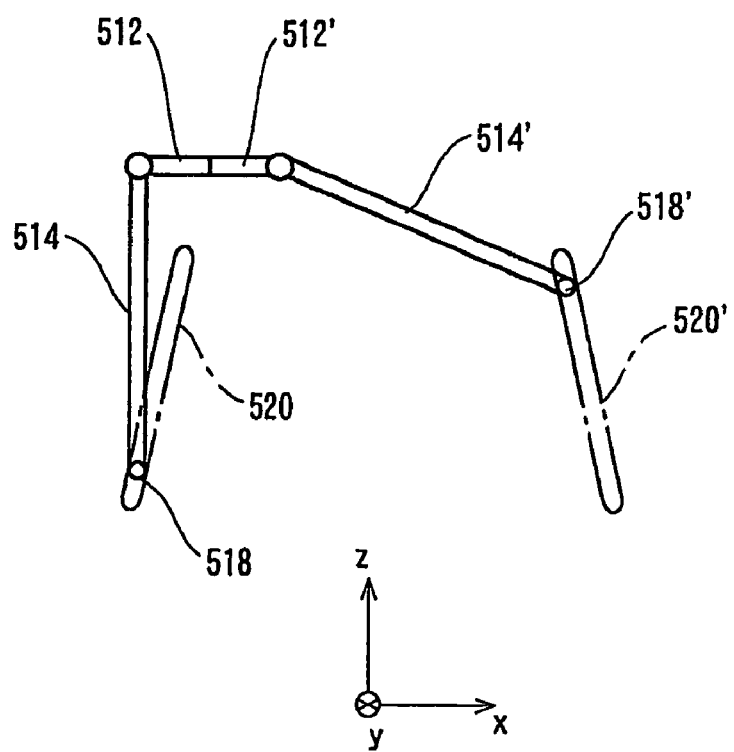
FIG. 8 illustrates adjusting the aperture.

By making end faces of the horizontal plates 512 and 512' come closely into contact with each other, the aperture can be fully closed, as shown in FIG. 7. The full closing of the aperture can also be done in an offset state of the horizontal plates 512 and 512', for example as shown in FIG. 8.

The follow-up plates 514 and 514' also move following the movement of the horizontal plates 512 and 512' to cover the other portion than the aperture. In this case, the movement of lower end portions of the follow-up plates 514 and 514' is restricted by the engagement of the pins 518 and 518' with the guide grooves 520 and 520', so that the movement of the follow-up plates 514 and 514' is restricted so that their lower ends move along the guide grooves 520 and 520'.

As a result, when the horizontal plates 512 and 512' are moved to be close to each other, the lower ends of the follow-up plates 514 and 514' rise along the guide grooves 520 and 520', while when the horizontal plates 512 and 512' are moved away from each other, the lower ends of the follow-up plates go down along the guide grooves 520 and 520'.

Figure 9:
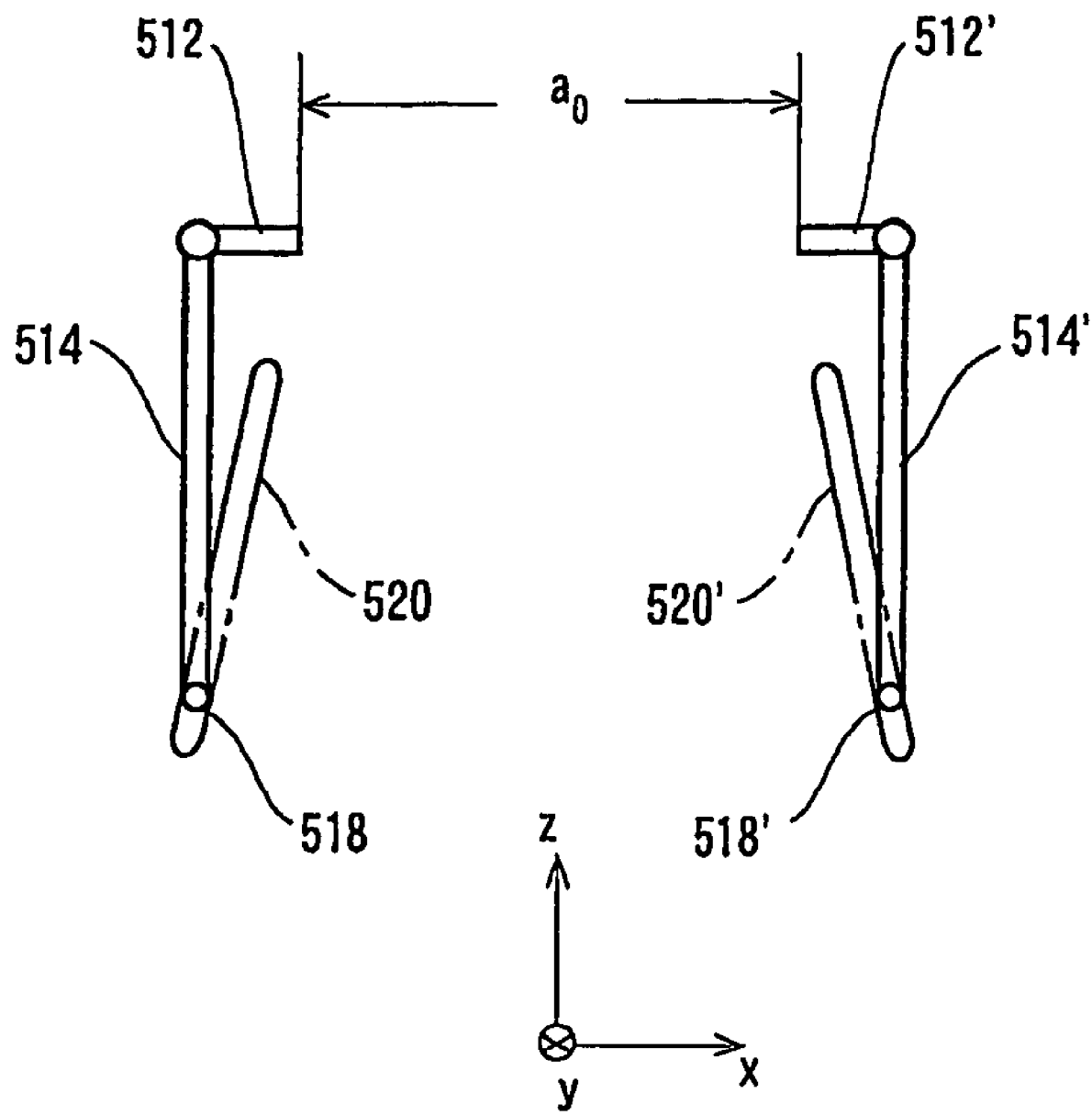
FIG. 9 illustrates adjusting the aperture.

When the horizontal plates 512 and 512' are moved to a maximum limit away from each other, the aperture becomes fully open. This state is shown in FIG. 9. As shown in the same figure, the horizontal plates 512 and 512' retreat to a maximum limit in the right and left direction to form a maximum aperture a0. At this time, the lower ends of the follow-up plates 514 and 514' assume a lowest state in the guide grooves 520 and 520'.

Thus, the lower ends of the follow-up plates 514 and 514' move obliquely along the guide grooves 520 and 520', so that even if the aperture is made fully open, the external shape of the collimating plate 500 does not become so large. Consequently, it is possible to reduce the size of the collimator 5 having the collimating plate 500 in the interior thereof. Besides, no special material is needed because the horizontal plates 512 and 512' and the follow-up plates 514 and 514' can each be fabricated using a lead plate or the like.

Many widely different embodiments of the invention may be configured without departing from the spirit and the scope of the present invention. It should be understood that the present invention is not limited to the specific embodiments described in the specification, except as defined in the appended claims.

The invention claimed is:

1. A collimator comprising:
a pair of first plate members, each first plate member having X-ray absorbability and movable in a direction parallel to an end surface thereof, each first plate member comprising an inner surface such that an X-ray passing aperture is defined by a space between the inner surfaces of the first plate members; and
a pair of second plate members, each second plate member having X-ray absorbability and comprising a top surface and an opposite bottom surface, each second plate member top surface connected to an outer surface of a respective first plate member via a hinge in order to block X-rays other than the X-rays passing through the X-ray passing aperture, each second plate member supported on a first end and an opposite second end such that each second plate member is movable obliquely in relation to movement of the respective first plate member and such that each second plate member moves with movement of the respective first plate member.

2. A collimator according to claim 1, wherein the first end and the second end of each of the second plate members are supported by guide grooves formed obliquely with respect to the moving direction of the first plate members and pins engaged in the guide grooves.

3. A collimator according to claim 1, wherein the pair of first plate members are movable independently of each other.

4. A collimator according to claim 1, further comprising a pair of arms and a pair of shafts, each arm coupling a first plate member to a respective shaft.

5. A collimator according to claim 4, wherein each arm is threadedly engaged with the respective shaft.

6. A collimator according to claim 1, further comprising a window plate positioned beneath the pair of second plate members, the window plate defining an aperture having at least one of a length that is greater than a width of the X-ray passing aperture and a length that is greater than a length of the X-ray passing aperture.

7. A collimator according to claim 1, wherein the pair of first plate members are movable such that the X-ray passing aperture one of maintains a desired width and changes width as the pair of first plate members moves.

8. An X-ray irradiator comprising:
an X-ray tube; and
a collimator for collimating X-rays generated from the X-ray tube, the collimator comprising:
a pair of first plate members, each first plate member having X-ray absorbability and movable in a direction parallel to an end surface thereof, each first plate member comprising an inner surface such that an X-ray passing aperture is defined by a space between the inner surfaces of the first plate members; and
a pair of second plate members, each second plate member having X-ray absorbability and comprising a top surface and an opposite bottom surface, each second plate member to surface connected to an outer surface of a respective first plate member via a hinge in order to block X-rays other than the X-rays passing through the X-ray passing aperture, each second plate member supported on a first end and an opposite second end such that each second plate member is movable obliquely in relation to movement of the respective first plate member and such that each second plate member moves with movement of the respective first plate member.

9. An X-ray irradiator according to claim 8, wherein the first end and the second end of each of the second plate members are supported by guide grooves formed obliquely with respect to the moving direction of the first plate members and pins engaged in the guide grooves.

10. An X-ray irradiator according to claim 8, wherein the pair of first plate members are movable independently of each other.

11. An X-ray irradiator according to claim 8, wherein the collimator further comprises a pair of arms and a pair of shafts, each arm coupling a first plate member to a respective shaft.

12. An X-ray irradiator according to claim 11, wherein each arm is threadedly engaged with the respective shaft.

13. An X-ray irradiator according to claim 8, wherein the collimator further comprises a window plate positioned beneath the pair of second plate members, the window plate defining an aperture having at least one of a length that is greater than a width of the X-ray passing aperture and a length that is greater than a length of the X-ray passing aperture.

14. An X-ray irradiator according to claim 8, wherein the pair of first plate members are movable such that the X-ray passing aperture one of maintains a desired width and changes width as the pair of first plate members moves.

15. An X-ray apparatus comprising:

an X-ray tube;

a collimator for collimating X-rays emitted from the X-ray tube and applying the collimated X-ray to an object to be radiographed, the collimator comprising:

a pair of first plate members, each first plate member having X-ray absorbability and movable in a direction parallel to an end surface thereof, each first plate member comprising an inner surface such that an X-ray passing aperture is defined by a space between the inner surfaces of the first plate members; and a pair of second plate members, each second plate member having X-ray absorbability and comprising a top surface and an opposite bottom surface, each second plate member top surface connected to an outer surface of a respective first plate member via a hinge in order to block X-rays other than the X-rays passing through the X-ray passing aperture, each second plate member supported on a first end and an opposite second end such that each second plate member is movable obliquely in relation to movement of the respective first plate member and such that each second plate member moves with movement of the respective first plate member; the X-ray apparatus further comprising a detector device for detecting X-rays that pass through the object to be radiographed.

16. An X-ray apparatus according to claim 15, wherein the first end and the second end of each of the second plate members are supported by guide grooves formed obliquely with respect to the moving direction of the first plate members and pins engaged in the guide grooves.

17. An X-ray apparatus according to claim 15, wherein the pair of first plate members are movable independently of each other.

18. An X-ray apparatus according to claim 15, wherein the collimator further comprises a pair of arms and a pair of shafts, each arm coupling a first plate member to a respective shaft.

19. An X-ray apparatus according to claim 18, wherein each arm is threadedly engaged with the respective shaft.

20. An X-ray apparatus according to claim 15, wherein the collimator further comprises a window plate positioned beneath the pair of second plate members, the window plate defining an aperture having at least one of a length that is greater than a width of the X-ray passing aperture and a length that is greater than a length of the X-ray passing aperture.

* * * * *